(12) United States Patent
Downer

(10) Patent No.: US 8,894,664 B2
(45) Date of Patent: Nov. 25, 2014

(54) LENS DELIVERY SYSTEM CARTRIDGE

(75) Inventor: David Downer, Fort Worth, TX (US)

(73) Assignee: Novartis AG, Basel (CH)

( * ) Notice: Subject to any disclaimer, the term of this patent is extended or adjusted under 35 U.S.C. 154(b) by 628 days.

(21) Appl. No.: 12/366,767

(22) Filed: Feb. 6, 2009

(65) Prior Publication Data

US 2009/0204123 A1 Aug. 13, 2009

Related U.S. Application Data

(60) Provisional application No. 61/026,805, filed on Feb. 7, 2008.

(51) Int. Cl.
*A61F 9/00* (2006.01)
*A61F 2/16* (2006.01)

(52) U.S. Cl.
CPC .................................. *A61F 2/1664* (2013.01)
USPC ....................................................... 606/107

(58) Field of Classification Search
USPC ........ 623/6.12, 17.16, 1.12; 606/107; 604/15, 604/57, 59, 60; 221/240, 156–173
See application file for complete search history.

(56) References Cited

U.S. PATENT DOCUMENTS

| | | | |
|---|---|---|---|
| 4,198,980 A | 4/1980 | Clark |
| 4,214,585 A | 7/1980 | Bailey, Jr. |
| 4,573,998 A | 3/1986 | Mazzocco |
| 4,600,003 A | 7/1986 | Lopez |
| 4,619,657 A | 10/1986 | Keates et al. |
| 4,681,102 A | 7/1987 | Bartell |
| 4,747,404 A | 5/1988 | Jampel et al. |
| 4,765,329 A | 8/1988 | Cumming et al. |
| 4,834,094 A | 5/1989 | Patton et al. |
| 4,836,201 A | 6/1989 | Patton et al. |
| 4,919,130 A | 4/1990 | Stoy et al. |
| 4,934,363 A | 6/1990 | Smith et al. |
| 4,955,889 A | 9/1990 | Van Gent |
| 4,960,557 A | 10/1990 | Sorensen |
| 4,988,352 A | 1/1991 | Poley |
| 5,007,913 A | 4/1991 | Dulebohn et al. |
| 5,026,396 A | 6/1991 | Darin |
| 5,098,439 A | 3/1992 | Hill et al. |
| 5,176,686 A | 1/1993 | Poley |

(Continued)

FOREIGN PATENT DOCUMENTS

AU 728443 1/2001
CN 101073519 11/2007

(Continued)

OTHER PUBLICATIONS

Ellipse, by J.B. Calvert, Denver University,website created on May 6, 2002.*

(Continued)

*Primary Examiner* — Tuan V Nguyen
(74) *Attorney, Agent, or Firm* — Darien Reddick

(57) ABSTRACT

A cartridge for an IOL delivery system that has an injector tip geometry designed to reduce stresses at the incision wound edges generated during insertion of an IOL into an eye is disclosed. The injector tip geometry includes a tubular nozzle having a modified elliptical cross section. The injector tip geometry reduces stresses generated reduce the likelihood of tearing or overstretching the wound during cartridge tip insertion and residence time in the wound while the lens is being delivered into the eye.

3 Claims, 4 Drawing Sheets

(56) References Cited

U.S. PATENT DOCUMENTS

| | | |
|---|---|---|
| 5,190,552 A | 3/1993 | Kelman |
| 5,195,526 A | 3/1993 | Michelson |
| 5,275,604 A | 1/1994 | Rheinish et al. |
| 5,290,892 A | 3/1994 | Namdaran et al. |
| 5,304,182 A | 4/1994 | Rheinish et al. |
| 5,354,333 A | 10/1994 | Kammann et al. |
| 5,397,313 A | 3/1995 | Gross |
| 5,425,734 A | 6/1995 | Blake |
| 5,444,183 A | 8/1995 | Gehrs et al. |
| 5,464,396 A | 11/1995 | Barta et al. |
| 5,468,246 A | 11/1995 | Blake |
| 5,474,562 A * | 12/1995 | Orchowski et al. ........... 606/107 |
| 5,494,484 A | 2/1996 | Feingold |
| 5,496,278 A | 3/1996 | Buff |
| 5,496,328 A | 3/1996 | Nakajima et al. |
| 5,499,987 A | 3/1996 | Feingold |
| 5,571,113 A | 11/1996 | McDonald |
| 5,578,042 A | 11/1996 | Cumming |
| 5,582,614 A | 12/1996 | Feingold |
| 5,607,433 A | 3/1997 | Polla et al. |
| 5,616,148 A | 4/1997 | Eagles et al. |
| 5,620,450 A | 4/1997 | Eagles et al. |
| 5,629,577 A | 5/1997 | Polla et al. |
| 5,643,275 A | 7/1997 | Blake |
| 5,643,276 A | 7/1997 | Zaleski |
| 5,653,715 A | 8/1997 | Reich et al. |
| 5,653,753 A | 8/1997 | Brady et al. |
| 5,716,364 A | 2/1998 | Makker et al. |
| 5,728,102 A | 3/1998 | Feingold et al. |
| 5,735,858 A | 4/1998 | Makker et al. |
| 5,772,666 A | 6/1998 | Feingold et al. |
| 5,776,138 A | 7/1998 | Vidal et al. |
| 5,800,441 A | 9/1998 | Polla et al. |
| 5,800,442 A | 9/1998 | Wolf et al. |
| 5,803,925 A | 9/1998 | Yang et al. |
| 5,810,834 A | 9/1998 | Heyman |
| 5,820,373 A | 10/1998 | Okano et al. |
| 5,860,986 A | 1/1999 | Reich et al. |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,891,153 A | 4/1999 | Peterson |
| 5,928,245 A | 7/1999 | Wolf et al. |
| 5,944,725 A | 8/1999 | Cicenas et al. |
| 5,947,976 A | 9/1999 | Van Noy et al. |
| 6,010,510 A | 1/2000 | Brown et al. |
| 6,042,587 A | 3/2000 | Polla et al. |
| 6,056,758 A | 5/2000 | Vidal et al. |
| 6,083,231 A | 7/2000 | Van Noy et al. |
| 6,140,602 A | 10/2000 | Costin |
| 6,143,001 A | 11/2000 | Brown et al. |
| 6,162,229 A | 12/2000 | Feingold et al. |
| 6,162,230 A | 12/2000 | Polla et al. |
| 6,179,843 B1 | 1/2001 | Weiler |
| 6,193,683 B1 | 2/2001 | Ludin et al. |
| 6,228,094 B1 | 5/2001 | Erdman |
| 6,241,737 B1 | 6/2001 | Feingold |
| 6,254,607 B1 | 7/2001 | Makker et al. |
| 6,312,433 B1 | 11/2001 | Butts et al. |
| 6,334,862 B1 | 1/2002 | Vidal et al. |
| 6,355,046 B2 | 3/2002 | Kikuchi et al. |
| 6,387,101 B1 | 5/2002 | Butts et al. |
| 6,398,789 B1 | 6/2002 | Capetan |
| 6,406,481 B2 | 6/2002 | Feingold et al. |
| 6,423,035 B1 | 7/2002 | Das et al. |
| 6,447,519 B1 | 9/2002 | Brady et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,503,275 B1 | 1/2003 | Cumming |
| 6,506,195 B2 | 1/2003 | Chambers et al. |
| 6,558,395 B2 | 5/2003 | Hjertman et al. |
| 6,592,591 B2 | 7/2003 | Polla et al. |
| 6,605,093 B1 | 8/2003 | Blake |
| 6,607,537 B1 | 8/2003 | Binder |
| 6,635,731 B2 | 10/2003 | Mentak |
| 6,666,871 B2 | 12/2003 | Klkuchi et al. |
| 6,685,740 B2 | 2/2004 | Figueroa et al. |
| 6,899,698 B2 | 5/2005 | Sams |
| 6,899,717 B2 | 5/2005 | Weber et al. |
| 6,923,815 B2 | 8/2005 | Brady et al. |
| 6,964,648 B2 | 11/2005 | Talling et al. |
| 6,976,989 B1 | 12/2005 | Vincent |
| 7,014,641 B2 | 3/2006 | Kobayashi et al. |
| 7,037,328 B2 | 5/2006 | Vincent |
| 7,042,180 B2 | 5/2006 | Terry et al. |
| 7,131,976 B2 | 11/2006 | Kobayashi et al. |
| 7,156,854 B2 | 1/2007 | Brown et al. |
| 7,156,855 B2 | 1/2007 | Oda |
| 7,189,218 B2 | 3/2007 | Lichtenberg |
| 7,217,274 B2 | 5/2007 | Meyer |
| 7,279,006 B2 | 10/2007 | Vincent |
| 7,357,426 B2 | 4/2008 | Bormioli |
| 7,422,604 B2 | 9/2008 | Vaquero et al. |
| 7,429,263 B2 | 9/2008 | Vaquero et al. |
| 2001/0007075 A1 | 7/2001 | Hjertman et al. |
| 2002/0151904 A1 | 10/2002 | Feingold et al. |
| 2003/0033013 A1 | 2/2003 | Callahan et al. |
| 2003/0040755 A1 | 2/2003 | Meyer |
| 2003/0135221 A1 | 7/2003 | Sabet |
| 2003/0139749 A1 | 7/2003 | Kikuchi et al. |
| 2003/0212406 A1 | 11/2003 | Kobayashi et al. |
| 2003/0212409 A1 | 11/2003 | Kobayashi et al. |
| 2004/0024361 A1 | 2/2004 | Fago et al. |
| 2004/0054374 A1 | 3/2004 | Weber et al. |
| 2004/0087896 A1 | 5/2004 | Wise et al. |
| 2004/0097954 A1 | 5/2004 | Meyer |
| 2004/0097956 A1 | 5/2004 | Oda |
| 2004/0147938 A1 | 7/2004 | Dusek et al. |
| 2004/0160575 A1 | 8/2004 | Ayton et al. |
| 2004/0199174 A1 | 10/2004 | Herberger et al. |
| 2004/0215207 A1 | 10/2004 | Cumming |
| 2004/0238392 A1 | 12/2004 | Peterson et al. |
| 2005/0049605 A1 | 3/2005 | Vaquero et al. |
| 2005/0049606 A1 | 3/2005 | Vaquero et al. |
| 2005/0065534 A1 | 3/2005 | Hohl |
| 2005/0143750 A1 | 6/2005 | Vaquero |
| 2005/0149056 A1 | 7/2005 | Rathert |
| 2005/0149057 A1 | 7/2005 | Rathert |
| 2005/0203619 A1 | 9/2005 | Altmann |
| 2005/0222578 A1 | 10/2005 | Vaquero |
| 2005/0222579 A1 | 10/2005 | Vaquero et al. |
| 2005/0283164 A1 | 12/2005 | Wu et al. |
| 2006/0066962 A1 | 3/2006 | Drobnik et al. |
| 2006/0085013 A1 | 4/2006 | Dusek et al. |
| 2006/0167466 A1 | 7/2006 | Dusek |
| 2006/0184181 A1 | 8/2006 | Cole et al. |
| 2006/0200167 A1 | 9/2006 | Peterson et al. |
| 2006/0229633 A1 | 10/2006 | Shepherd |
| 2006/0229634 A1 | 10/2006 | Shepherd |
| 2006/0235429 A1 | 10/2006 | Lee et al. |
| 2006/0284581 A1 | 12/2006 | Mullin et al. |
| 2006/0287655 A1 * | 12/2006 | Khuray et al. ................. 606/107 |
| 2007/0005135 A1 | 1/2007 | Makker et al. |
| 2007/0050023 A1 | 3/2007 | Bessiere et al. |
| 2007/0060925 A1 | 3/2007 | Pynson |
| 2007/0173860 A1 | 7/2007 | Iwasaki |
| 2007/0270945 A1 | 11/2007 | Kobayashi et al. |
| 2008/0033449 A1 | 2/2008 | Cole et al. |
| 2008/0039862 A1 | 2/2008 | Tran |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0097461 A1 | 4/2008 | Boukhny et al. |
| 2008/0119865 A1 | 5/2008 | Meunier et al. |
| 2008/0200920 A1 | 8/2008 | Downer |
| 2008/0200921 A1 | 8/2008 | Downer |
| 2008/0221584 A1 | 9/2008 | Downer |
| 2008/0221585 A1 | 9/2008 | Downer |
| 2008/0255577 A1 | 10/2008 | Downer |
| 2009/0043313 A1 | 2/2009 | Ichinohe et al. |

(56) References Cited

U.S. PATENT DOCUMENTS

| | | | |
|---|---|---|---|
| 2009/0112223 A1 | 4/2009 | Downer |
| 2009/0171366 A1 | 7/2009 | Tanaka |
| 2009/0204123 A1 | 8/2009 | Downer |
| 2009/0216244 A1 | 8/2009 | Pynson |

FOREIGN PATENT DOCUMENTS

| | | |
|---|---|---|
| DE | 4301573 | 7/1994 |
| DE | 19544119 | 5/1997 |
| DE | 20219445 | 3/2003 |
| EP | 0174917 | 3/1986 |
| EP | 0270257 | 6/1988 |
| EP | 0363213 | 4/1990 |
| EP | 0477466 | 6/1996 |
| EP | 0858304 | 8/1998 |
| EP | 0962195 | 12/1999 |
| EP | 1011561 | 6/2000 |
| EP | 1075826 A1 | 2/2001 |
| EP | 1076408 | 2/2001 |
| EP | 1332731 | 8/2003 |
| EP | 1360944 | 11/2003 |
| EP | 1481652 | 12/2004 |
| EP | 1661533 | 5/2006 |
| EP | 1832247 | 9/2007 |
| EP | 1849436 | 10/2007 |
| EP | 1857076 | 11/2007 |
| EP | 1891911 | 2/2008 |
| EP | 1941846 | 7/2008 |
| EP | 1958593 | 8/2008 |
| EP | 1958594 | 8/2008 |
| EP | 2062552 | 5/2009 |
| FR | 2820633 A1 | 8/2002 |
| GB | 1274949 | 5/1972 |
| GB | 2224214 | 5/1990 |
| GB | 2333460 | 7/1999 |
| JP | 1176288 | 12/1989 |
| JP | 5-103808 | 4/1993 |
| JP | 3664444 | 4/1994 |
| JP | 10309294 | 11/1998 |
| JP | 10511876 | 11/1998 |
| JP | 10512460 | 11/1998 |
| JP | 2000025073 | 1/2000 |
| JP | 2000-513955 | 10/2000 |
| JP | 2003070829 | 3/2003 |
| JP | 2003325569 | 11/2003 |
| JP | 2005-110924 | 4/2005 |
| JP | 2006014962 | 1/2006 |
| JP | 2006181269 | 7/2006 |
| JP | 2007055057 | 3/2007 |
| JP | 2007-307168 | 11/2007 |
| JP | 2007-319539 | 12/2007 |
| RU | 2138232 | 9/1999 |
| RU | 2171100 | 7/2001 |
| RU | 2238283 | 10/2004 |
| RU | 2242956 | 12/2004 |
| RU | 2379010 | 1/2010 |
| SU | 1440496 | 11/1988 |
| SU | 1706614 | 1/1992 |
| SU | 1814870 | 5/1993 |
| WO | 9420027 | 9/1994 |
| WO | 9603924 | 2/1996 |
| WO | 9610372 | 4/1996 |
| WO | 9620662 | 7/1996 |
| WO | 9628122 | 9/1996 |
| WO | 9629956 | 10/1996 |
| WO | 9715253 | 5/1997 |
| WO | 9726841 | 7/1997 |
| WO | 9805281 | 2/1998 |
| WO | 9812969 | 4/1998 |
| WO | 9815244 | 4/1998 |
| WO | 9820819 | 5/1998 |
| WO | 0040175 | 7/2000 |
| WO | 0062712 | 10/2000 |
| WO | 0139701 | 6/2001 |
| WO | 02060338 | 8/2002 |
| WO | WO 02 083216 | 10/2002 |
| WO | 02100468 | 12/2002 |
| WO | 2004091447 | 10/2004 |
| WO | 2006007303 | 1/2005 |
| WO | 2005018515 | 3/2005 |
| WO | 2005020853 | 3/2005 |
| WO | 2005023154 | 3/2005 |
| WO | 2005102223 | 11/2005 |
| WO | 2006059183 | 6/2006 |
| WO | 2006070561 | 7/2006 |
| WO | 2006080191 | 8/2006 |
| WO | 2006113138 | 10/2006 |
| WO | 2006113357 | 10/2006 |
| WO | 2007037223 | 4/2007 |
| WO | 2007080868 | 7/2007 |

OTHER PUBLICATIONS

International Search Report for PCT/US2009/033401, Publication No. WO2009/100337, 4 pages, dated Jun. 18, 2009.

European Search Report for Application No. 08102185.9, Publication No. EP2002803, Published Dec. 17, 2008, dated Apr. 25, 2008, 3 pages.

PCT International Preliminary Report on Patentability and Written Opinion of the International Searching Authority, International Application No. PCT/US2009/033401, dated Aug. 10, 2010, 5 pages.

European Search Report for Application No. 08102172.7, Publication No. 1980219, dated Oct. 15, 2008, 5 pages.

Abstract of article entitled "Implantation of the AcrySof MA30BA lens using the Monarch System" by Barakova D., original article found in Cesk slov Oftalmol, 2002 58(3), at p. 149-152, found in PubMed database at http://www.ncbi.nlm.nih.gov/pubmed/12087658 (1 page).

International Search Report for PCT/US2010/037374, dated Sep. 3, 2010, 3 pages.

Written Opinion for PCT/US2010/037374, dated Sep. 3, 2010, 7 pages.

* cited by examiner

|  | ArcLength (mm) | ArcLength/Width |
|---|---|---|
| Circle in Quadrant I | 1.492 | 1.571 |
| Ellipse in Quadrant I | 1.318 | 1.387 |
| Line in Quadrant I | 1.192 | 1.255 |

LENS DELIVERY SYSTEM CARTRIDGE

This application claims priority under 35 USC §119 to U.S. provisional application Ser. No. 61/026,805, filed on Feb. 7, 2008.

This invention relates to intraocular lenses (IOLs) and more particularly to cartridges for use with devices used to inject IOLs into an eye.

BACKGROUND OF THE INVENTION

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens.

When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens or IOL.

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. The most commonly used injector cartridge design is illustrated in U.S. Pat. No. 4,681,102 (Bartell), and includes a split, longitudinally hinged cartridge. Similar designs are illustrated in U.S. Pat. Nos. 5,494,484 and 5,499,987 (Feingold) and U.S. Pat. Nos. 5,616,148 and 5,620,450 (Eagles, et al.). In an attempt to avoid the claims of U.S. Pat. No. 4,681,102, several solid cartridges have been investigated, see for example U.S. Pat. Nos. 5,275,604 (Rheinish, et al.) and U.S. Pat. No. 5,653,715 (Reich, et al.).

These prior art devices were intended to inject an IOL into the posterior chamber of an aphakic eye through a relatively large (approximately 3.0 mm or larger) incision. Surgical techniques and IOLs have been developed that allow the entire surgical procedure to be performed through much smaller incisions, 2.4 mm and smaller. Such small incisions require that the IOL be compressed very tightly, and that the nozzle used on the injection cartridge have very thin walls. The combination of a tightly compressed lens traveling through a very thin walled nozzle often results in the nozzle splitting during use. In addition, although the surgeon may make the incision a specific size, insertion and manipulation of the cartridge and the lens frequently stresses the incision walls, increasing the size of the incision as well as causing trauma to the surrounding tissue.

Accordingly, a need continues to exist for an intraocular lens injection cartridge capable of injection an IOL through a relatively small incision with reduced trauma to the tissue.

BRIEF SUMMARY OF THE INVENTION

The present invention improves upon the prior art by providing a cartridge for an IOL delivery system that has a injector tip geometry designed to reduce applied stresses on the incision during insertion of the cartridge tip through the wound to reduce the likelihood of tearing or overstretching the wound during cartridge tip insertion and residence time in the wound while the lens is being delivered into the eye.

It is accordingly an objective of the present invention to provide a cartridge for a lens delivery system that has an injector tip geometry designed to reduce stresses on the wound incision.

It is a further objective of the present invention to provide a cartridge for a lens delivery system that reduces post insertion wound trauma.

Other objectives, features and advantages of the present invention will become apparent with reference to the drawings, and the following description of the drawings and claims.

DETAILED DESCRIPTION OF THE PREFERRED EMBODIMENTS

The present invention is directed to cartridge 10 having a body 11 and tip 12, tip 12 having a geometry designed to reduce stresses generated during insertion of an IOL into an eye. Although any incision size can be used, the dimensions given in the following discussion are based on a 2.0 mm incision or wound in the eye.

The action of inserting a cartridge tip 12 through an incision wound develops stresses at the wound edges that can result in trauma and tearing of the incision. The inventors have discovered that a correlation exists between the degree of wound stresses and cartridge tip geometry. Based on this discovery, the inventors determined that the incision or wound can be modeled as a deformable body having roughly an elliptical outer dimension with a major axis of approximately 2.0 mm and a minor axis of approximately 0.25 mm. In addition, the inventors determined that a cartridge tip 12 nozzle can be modeled as a rigid body with the assumption that no deformation of the tip 12 nozzle occurs during the insertion of an IOL into an eye and that any deformation occurs in the wound. As no actual tissue material properties are available, the material properties of the wound tissue can be modeled using the Arruda-Boyce material model. Assuming that the area of the tip 12 nozzle is larger than the area of the wound, the inventors applied a theoretical load to the inside of the wound to "stretch" the wound large enough to allow the nozzle tip 12 to enter. By lowering the theoretical load until the interior wound margins contact the entire outer peripheral surface of the tip 12, the residual strain, stress, stress distribution and contact pressure can be determined.

Figure 1:
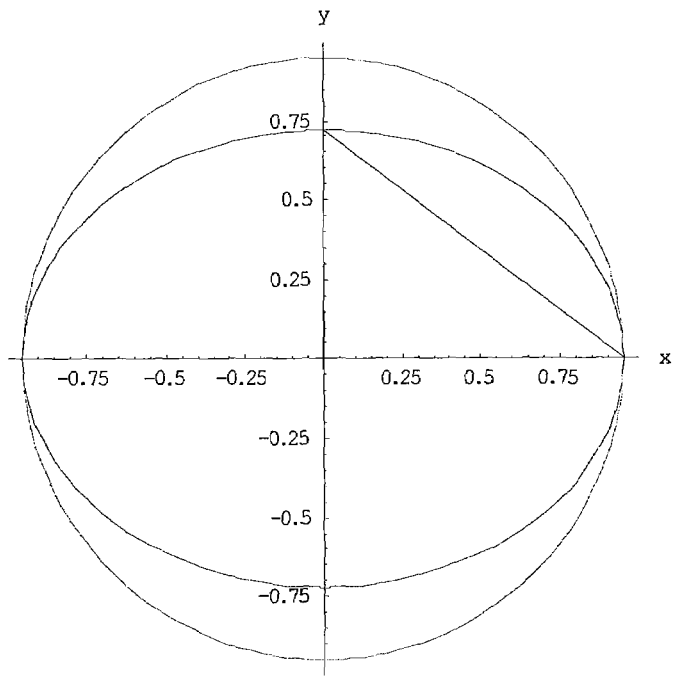
FIG. 1 is a graph comparing the arc length for a circle, an ellipse and a straight line.

One skilled in the art understands that a circle or round cartridge tip has an aspect ratio of 1 because the height and width are equal. However, as the aspect ratio is reduced by shortening the height, the arc length changes which serves to reduce the degree of wound stretching by reducing the applied stresses at the wound edges as shown in FIG. 1. One skilled in the art also understands that a straight line connecting height and width results in the shortest distance between those points and represents the shortest "arc" length possible relative to applied stresses on the wound without creating a negative arc. Negative arc is undesirable because lens damage or undesirable folding can occur when a negative arc or non-curved geometry is used.

Figure 2:
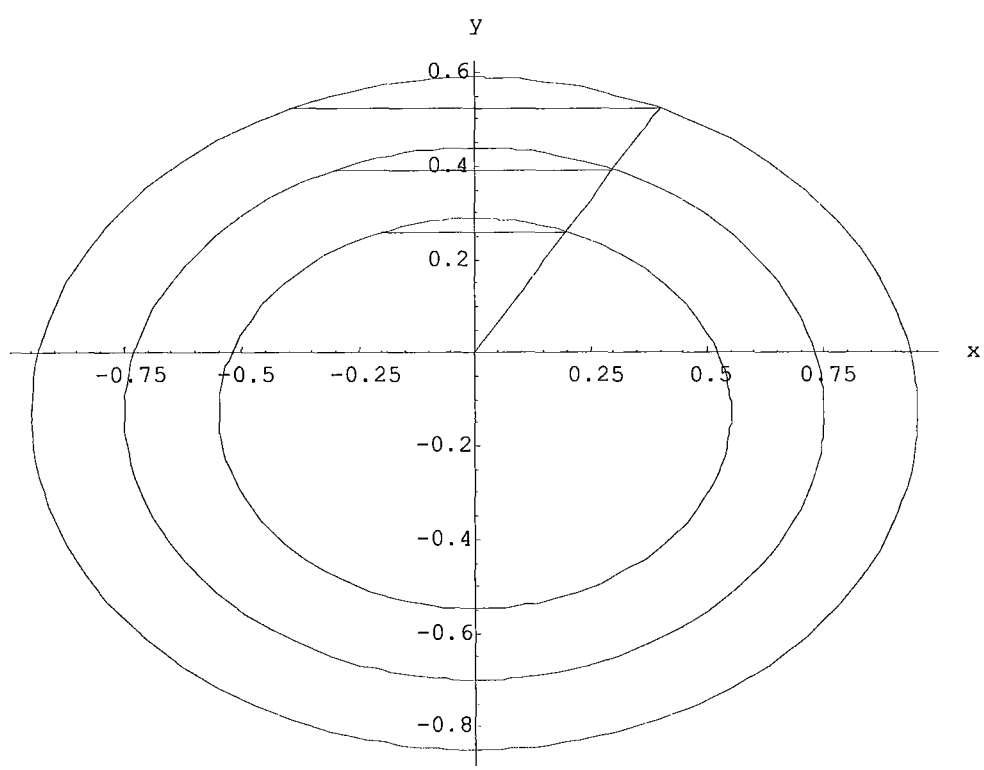
FIG. 2 is a graph illustrating theoretical incision size for various tip sizes.
Figure 3:
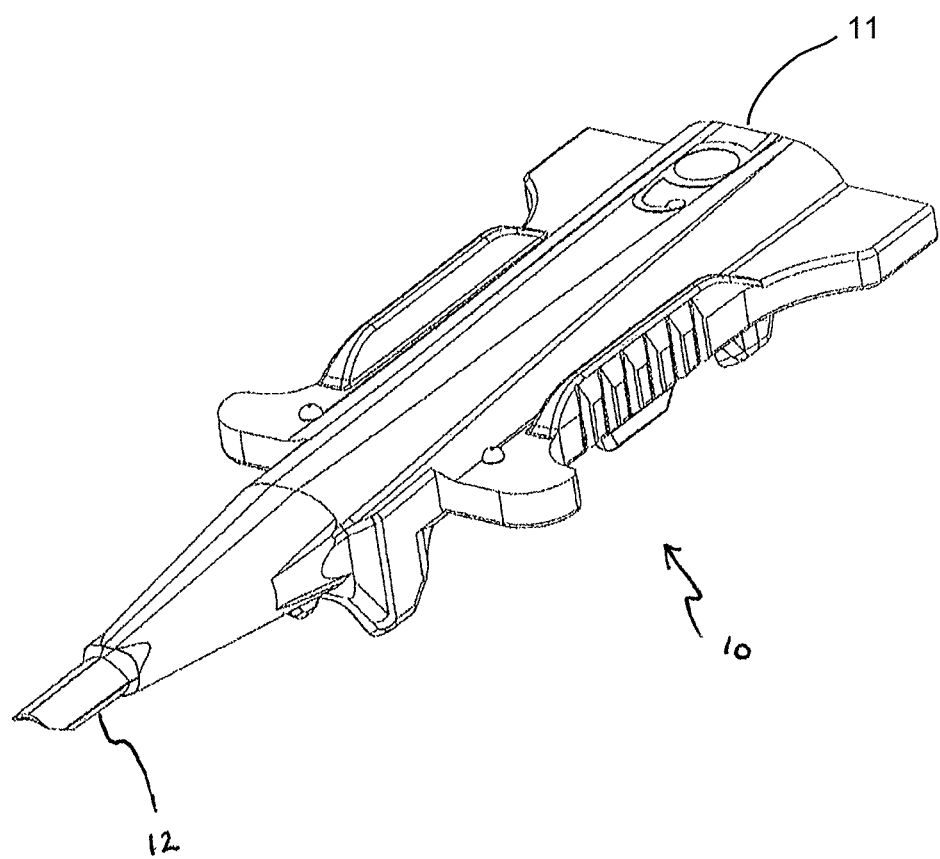
FIG. 3 is an enlarged perspective view of the lens delivery system cartridge of the present invention.

The cross-sectional form of an ellipsoid, representing the injection tip 12 geometry, can be analyzed by using the ellipse shape factor. This shape factor 'ϵ' can remain constant to maintain the same form as the tip size is varied from 3.0 mm and below. By varying other parameter values, the form is maintained while reducing the periphery and resultant theoretical incision size as shown in Table 1 below and FIG. 2.

Figure 4:
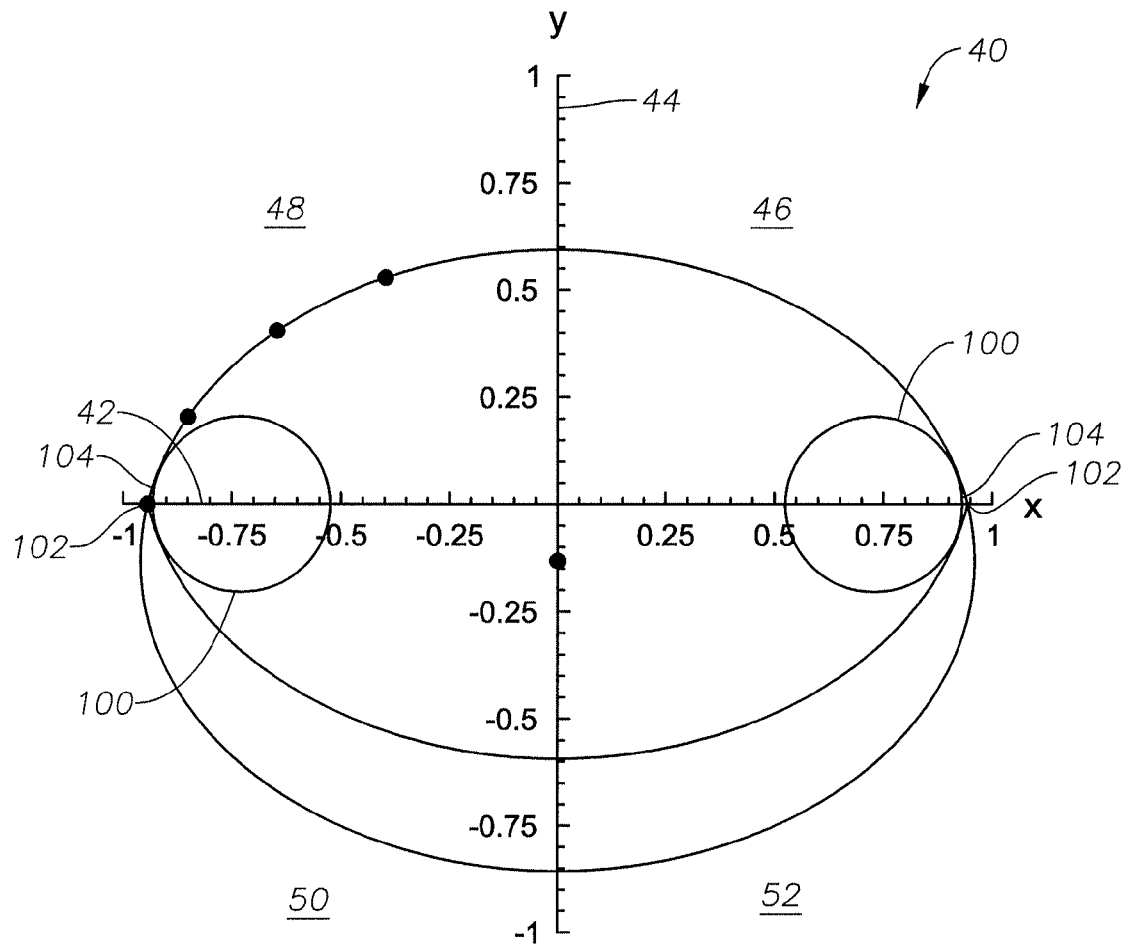
FIG. 4 is a graph illustrating a circle used to form a blend radius for forming a modified elliptical cross-sectional shape of an injection tip, where the circle is tangent to both a curve above and below an inflection point and that has a 90 degree tangent line at a point crossing the x-axis.

FIG. 4 shows a Cartesian coordinate system 40 having an abscissa axis (interchangeably referred to as "x-axis") 42 and an ordinate axis (interchangeably referred to as "y-axis") 44. The Cartesian coordinate system 40 defines a first quadrant (also referred to as quadrant I) 46, a second quadrant (also referred to as quadrant II) 48, a third quadrant (also referred to as quadrant III) 50, and a fourth quadrant (also referred to as quadrant IV) 52.

This shape factor ϵ, also known as eccentricity, is further discussed below starting with the ellipse equation. A cross section of an ellipsoid in a plane parallel to coordinate axes forms an ellipse. In general, this 2D ellipse can be represented by the following equation:

$$\frac{(x-h)^2}{a^2} + \frac{(y-k)^2}{b^2} = 1;$$

Where h, k represent the center of the ellipse, 'a' is the major axis and 'b' the minor axis. The shape of an ellipse can be represented by its eccentricity, ϵ, defined as follows:

$$\epsilon = (1/a)(\sqrt{a^2-b^2});$$

where $0 < \epsilon < 1$. The larger the value of ϵ is, the larger the ratio of a to b and the more elongated the ellipse becomes. Furthermore, for a given eccentricity value, if we know parameter 'a' or 'b' then the other parameter can be easily calculated using this equation. For completion, note that parameters 'a' and 'b' are constrained by the following equation:

$$c^2 = a^2 - b^2;$$

where '(±c,0)' represent the foci of the ellipse. Note that the cross section of the ellipse is modified in the sense that the center of the ellipse is not necessarily at the origin and is allowed to float. For example, FIG. 4 shows ellipse 54 having center 56. FIG.4 shows the center 56 located along the negative portion of the y-axis 44. However, allowing for de-centration of the ellipse leaves a point of inflection 102 (shown in FIG. 4), a sharp feature, when the part of the ellipse lying in quadrant I 46 is revolved around the x-axis 42. To smooth out this point, a blend in radius is used so that the tangent to the point intersecting the x-axis is at 90 degrees. These two features, the decentered ellipse as well as a blend radius 104 constitute the cross section of the modified ellipsoid configuration.

An alternate form to the above ellipse equation can be represented as, $$Ax^2 + Bxy + Cy^2 + Dx + Ey + F = 0;$$

where $B^2 < 4AC$ and all coefficients are real. This equation can be converted to the first equation by completing squares and obtaining a form that displays the center of the ellipse as well as the lengths of major and minor axes.

Using the above guidelines, these parameters can be calculated. The elliptic curve in quadrant 1 was fitted to a general ellipse and it was found that (h, k)=(0.0,−0.13), and (a, b)= (0.95, 0.72). The eccentricity ϵ was then calculated to be 0.65. Given this eccentricity, if either of the two axial dimensions of the ellipse is to be changed, then the other can be calculated with the above equation. Generally, the blend radius at the point of inflection can be chosen to be the smallest possible circle that is tangent to both the curve above and below and has a 90 deg. tangent line at the point crossing the x-axis, such as circle 100 of FIG. 4.

An example of the application of the determined minimum arc length, aspect ratio and blend radius described above can be seen in Table 1 below where typical values for each of the variables are shown. The table defines typical modified ellipsoid values as a function of incision size. Incision sizes of 1.0, 2.0 and 3.0 mm are used to demonstrate the relationship when the ArcLength width and Ellipse eccentricity are held constant. Applying these values to cartridge tip designs result in the maximum internal volume relative to the minimum arc length which in combination results in significantly reduced strain at the incision wound edges while minimizing the degree of lens compression and resultant lens injection forces.

TABLE 1

Modified Ellipsoid typical dimensions as a function of Incision size.

| Incision Size (mm) | Ellipse Major Axis, a (mm) | Ellipse Minor Axis, b (mm) | Ellipse Eccentricity, ϵ | ArcLength (mm) | ArcLength/ Width | Blend Radius (mm) |
|---|---|---|---|---|---|---|
| 1.0 | 0.392 | 0.30 | 0.65 | 1.087 | 1.386 | 0.2 |
| 2.0 | 0.784 | 0.60 | 0.65 | 2.174 | 1.386 | 0.4 |
| 3.0 | 1.176 | 0.90 | 0.65 | 3.261 | 1.386 | 0.6 |

The steps outlined above result in a design for cartridge tip 12 that provides the maximum internal volume relative to the minimum arc length. This combination results in significantly reduced strain at the incision wound edges while minimizing the degree of lens compression and resultant lens injection forces. The invention described within provides injector cartridge 10 or nozzle tip 12 shape that reduces the force required to insert cartridge tip 12 through the wound due to the reduced aspect ratio and arc length. In addition, this curved form facilitates reduced wound trauma and potential for lens damage through elimination of sharp external and internal features or transition points.

While certain embodiments of the present invention have been described above, these descriptions are given for purposes of illustration and explanation. Variations, changes, modifications and departures from the systems and methods disclosed above may be adopted without departure from the scope or spirit of the present invention.

I claim:

1. An intraocular lens delivery system cartridge, comprising:
 a body, and
 a tubular nozzle connected to the body and projecting distally from the body, the nozzle having a cross-section, the cross-section having a shape defined by:
  a portion of an ellipse disposed in a first quadrant and a second quadrant of a Cartesian coordinate system, the ellipse having a center that is offset from the origin of the Cartesian coordinate system in a direction along a negative portion of an ordinate axis of the Cartesian coordinate system, the portion of the ellipse defined as a first curve; and
  a second curve defined as a mirror image of the first curve mirrored about an abscissa axis of the Cartesian coordinate system, the first curve and the second curve forming first and second points at locations where the first curve and the second curve intersect the abscissa axis of the Cartesian coordinate system; and
  circular arcs formed at opposing ends of the cross-section proximate the first and second points, each circular arc defined as a portion of a circle joining the first curve and the second curve that is tangent to both the first curve and the second curve and that has a 90 degree tangent line at a point along the abscissa axis crossed by the circular arc.

2. The cartridge of claim 1, wherein the ellipse has an ellipse eccentricity of 0.65.

3. The cartridge of claim 1, wherein a distance defined along the abscissa axis between locations where the circular arcs intersect the abscissa axis defines a width of the cross-section,
 wherein a portion of the cross-section comprises a portion of one of circular arcs extending from the abscissa axis to the first curve, a portion of the first curve extending between the circular arcs, and a portion of the other of the circular arcs extending from the first curve to the abscissa axis,
 wherein a length of the portion of the cross-section defines an arc length, and
 wherein a ratio of the arc length to the width of the cross-section is 1.386.

* * * * *